(12) United States Patent
Wang (10) Patent No.: US 11,207,203 B2
(45) Date of Patent: Dec. 28, 2021

(54) ADJUSTABLE NECK BRACE

(71) Applicant: Yu-Chien Wang, Taichung (TW)

(72) Inventor: Yu-Chien Wang, Taichung (TW)

(*) Notice: Subject to any disclaimer, the term of this patent is extended or adjusted under 35 U.S.C. 154(b) by 317 days.

(21) Appl. No.: 16/558,644

(22) Filed: Sep. 3, 2019

(65) Prior Publication Data
US 2019/0388262 A1    Dec. 26, 2019

Related U.S. Application Data

(62) Division of application No. 15/198,335, filed on Jun. 30, 2016, now Pat. No. 10,463,524.

(51) Int. Cl.
*A61F 5/055*    (2006.01)

(52) U.S. Cl.
CPC .................... *A61F 5/055* (2013.01)

(58) Field of Classification Search
CPC .. A61F 5/055; A61F 5/04; A61F 5/042; A61F 5/048; A61F 5/05; A61F 5/05883; A61F 5/05816; A61F 5/05833
USPC .......................................................... 602/18
See application file for complete search history.

(56) References Cited

U.S. PATENT DOCUMENTS

| | | | | |
|---|---|---|---|---|
| 2012/0130295 | A1* | 5/2012 | Haider | A61F 5/055 602/18 |
| 2012/0165712 | A1* | 6/2012 | Calabrese | A61F 5/055 602/18 |
| 2013/0261519 | A1* | 10/2013 | Garth | A61F 5/055 602/18 |
| 2013/0281900 | A1* | 10/2013 | Suarez | A61F 5/055 602/18 |
| 2013/0310722 | A1* | 11/2013 | Thorsteinsdottir | A61F 5/05883 602/18 |
| 2015/0190266 | A1* | 7/2015 | Hollern | A61F 5/055 602/18 |
| 2016/0008158 | A1* | 1/2016 | Martin | A61F 5/055 602/18 |
| 2016/0058601 | A1* | 3/2016 | Garth | A61F 5/055 602/18 |

* cited by examiner

*Primary Examiner* — Tarla R Patel
(74) *Attorney, Agent, or Firm* — Muncy, Geissler, Olds & Lowe, P.C.

(57) ABSTRACT

An adjustable neck brace is provided, including: a neck collar, including a sliding engaging groove, the sliding engaging groove extending in an extension direction and having a first engaging portion; a single positioning member, attached to the neck collar and movable along the sliding engaging groove, having a second engaging portion, the second engaging portion being releasably positioningly engaged with the first engaging portion; a chin support, relatively movably connected to the neck collar; at least one connecting member, connecting the positioning member and the chin support.

3 Claims, 9 Drawing Sheets

ADJUSTABLE NECK BRACE

The present invention is a Divisional application of application Ser. No. 15/198,335, filed Jun. 30, 2016, the entire contents of which are hereby incorporated by reference.

BACKGROUND OF THE INVENTION

Field of the Invention

Description of the Prior Art

Generally, a neck brace is used to positioningly fix the cervical vertebra of a patient to prevent the patient from suffering from repeated injuries when moving around. However, relative positions of a neck collar and a chin support of the common neck brace cannot be adjusted according to various requirements, and it is inconvenient. Therefore, an adjustable neck brace structure is provided.

However, in a common adjustable brace, adjusting structures are disposed on two sides of the adjustable brace, so the two adjustable structures need to be adjusted simultaneously so as to adjust or position relative positions of a positioning neck collar and a chin support, and it is hard to adjust the adjusting structures to a same height synchronously. In addition, the patient may suffer from repeated injuries if the two sides of the neck brace are in different heights.

The present invention has arisen to mitigate and/or obviate the afore-described disadvantages.

SUMMARY OF THE INVENTION

The major object of the present invention is to provide an adjustable neck brace which can be stably adjusted into a most appropriate state through just one adjustment.

To achieve the above and other objects, an adjustable neck brace is provided, including: a neck collar, including a sliding engaging groove, the sliding engaging groove extending in an extension direction and having a first engaging portion; a single positioning member, attached to the neck collar and movable along the sliding engaging groove, having a second engaging portion, the second engaging portion being releasably positioningly engaged with the first engaging portion; a chin support, relatively movably connected to the neck collar; at least one connecting member, connecting the positioning member and the chin support.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Figure 1:
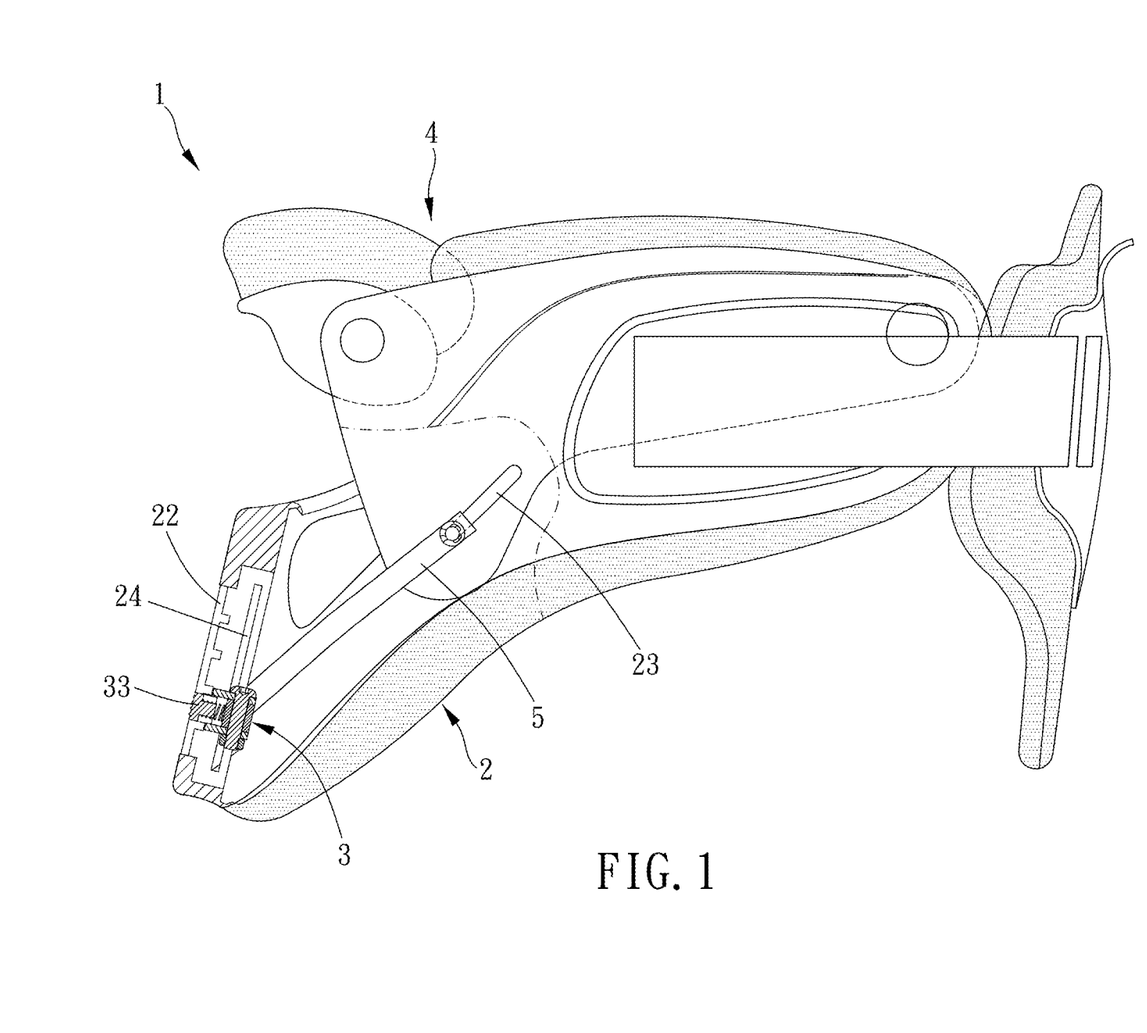
FIGS. 1 and 2 are partially cross-sectional views showing a preferred embodiment of the present invention in operation.
Figure 2:
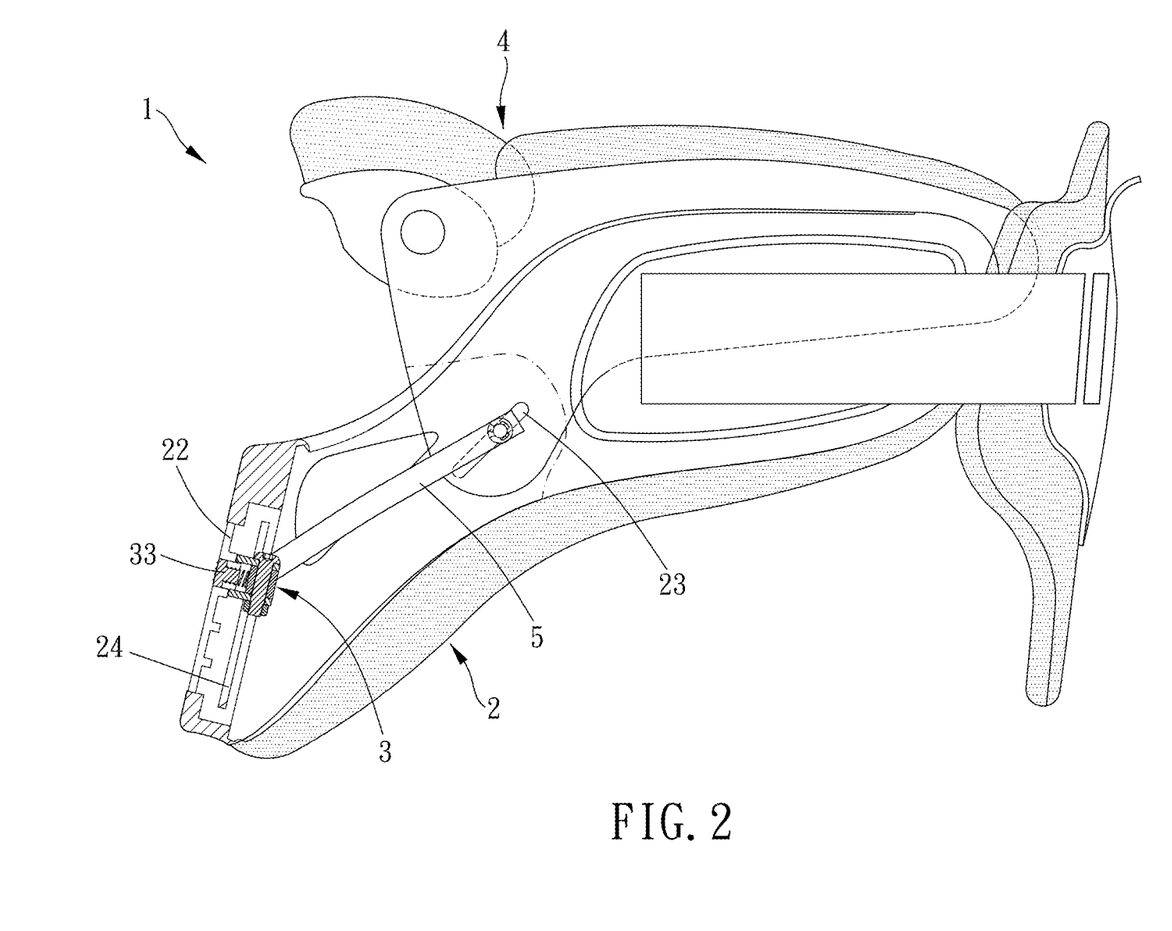
Figure 3:
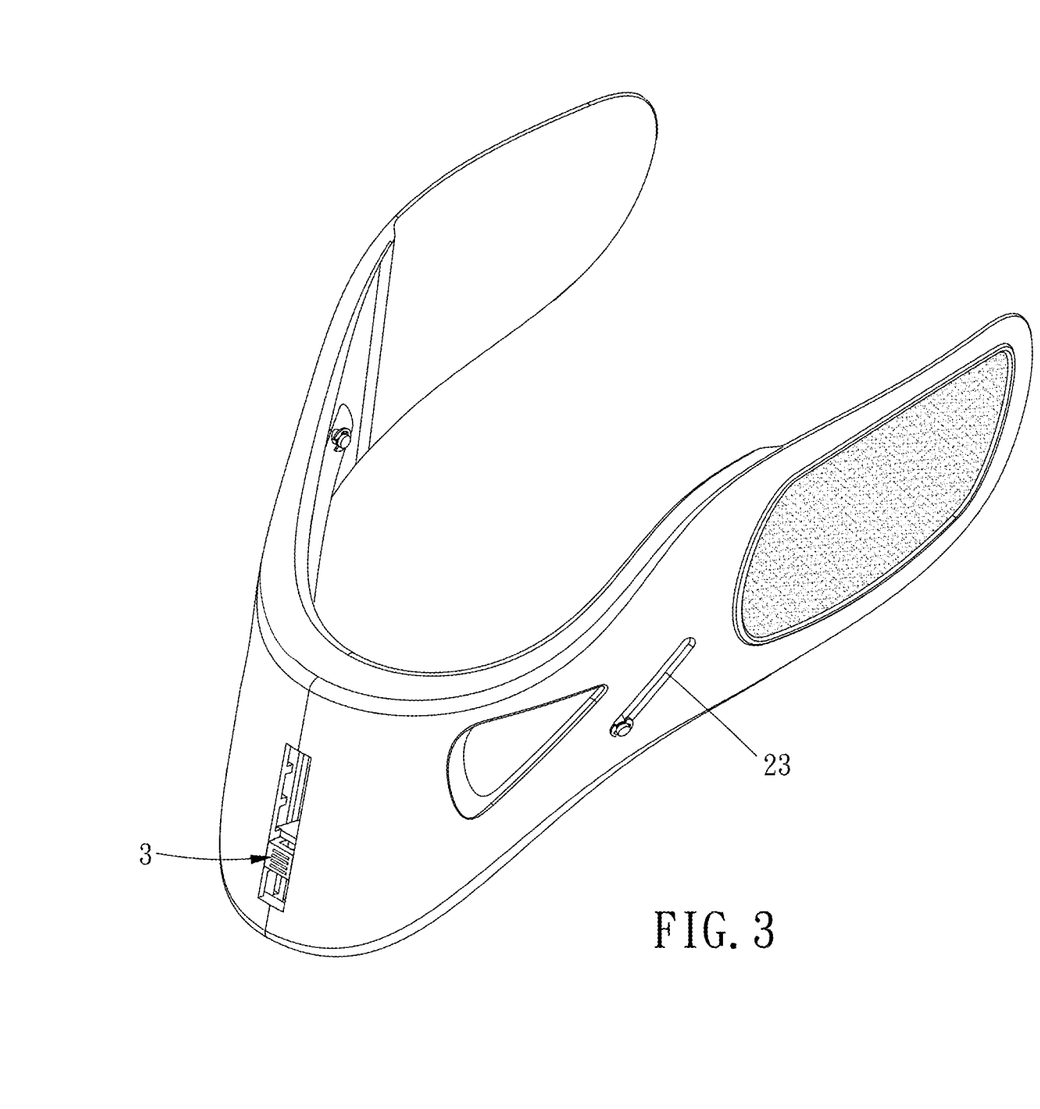
FIG. 3 is a drawing showing a part of the preferred embodiment of the present invention.
Figure 4:
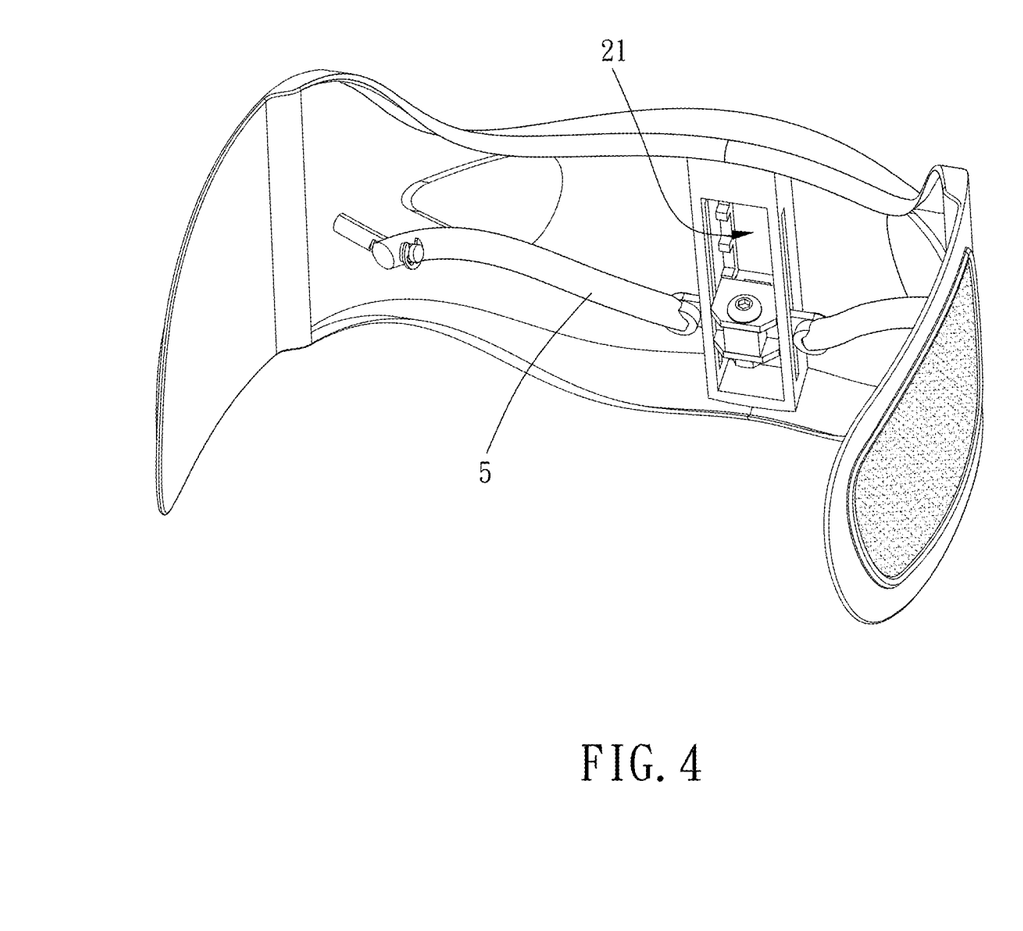
FIG. 4 is a drawing showing FIG. 3 from another perspective.
Figures 5, 6:
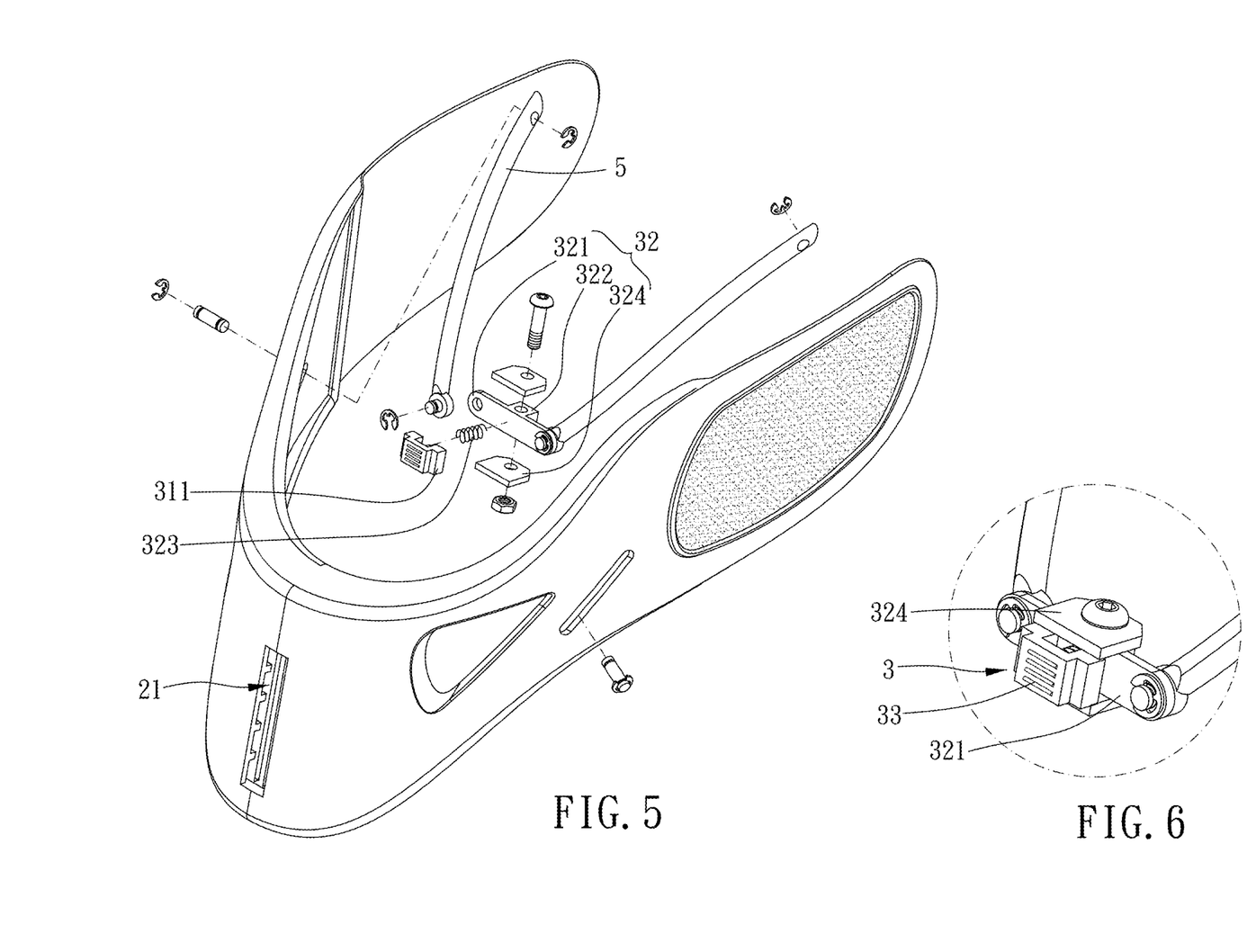
FIG. 5 is a breakdown stereogram of the preferred embodiment of the present invention.
FIG. 6 is an enlarged view of a positioning member of the preferred embodiment of the present invention.
Figure 7:
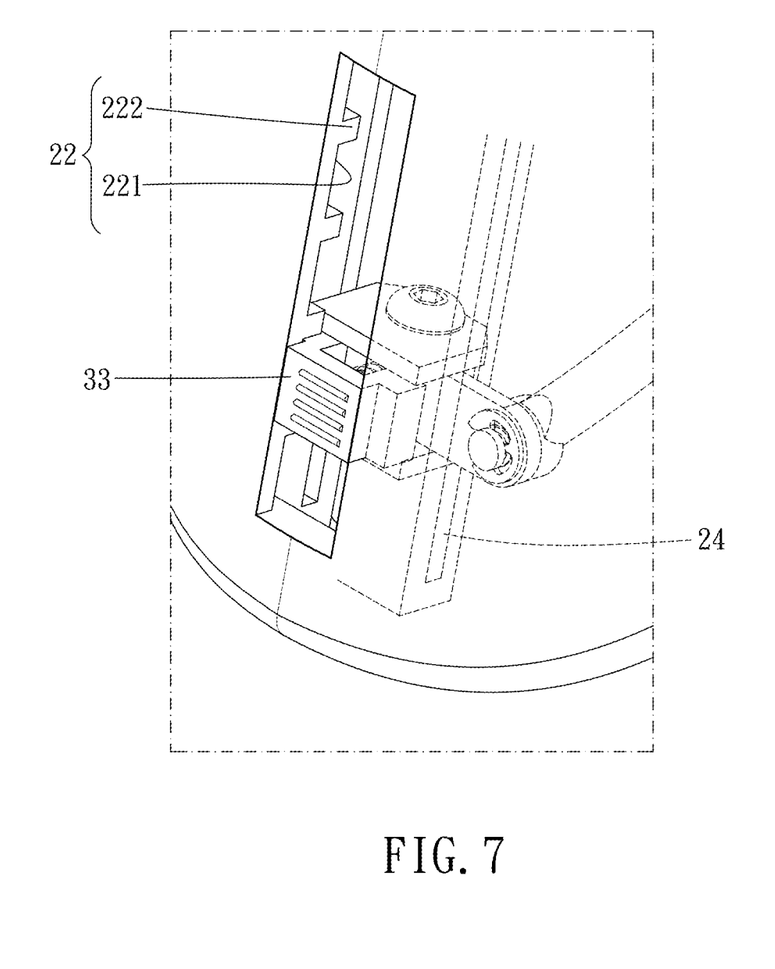
FIGS. 7 and 8 are partially-enlarged perspective views showing the preferred embodiment of the present invention in operation.
Figure 8:
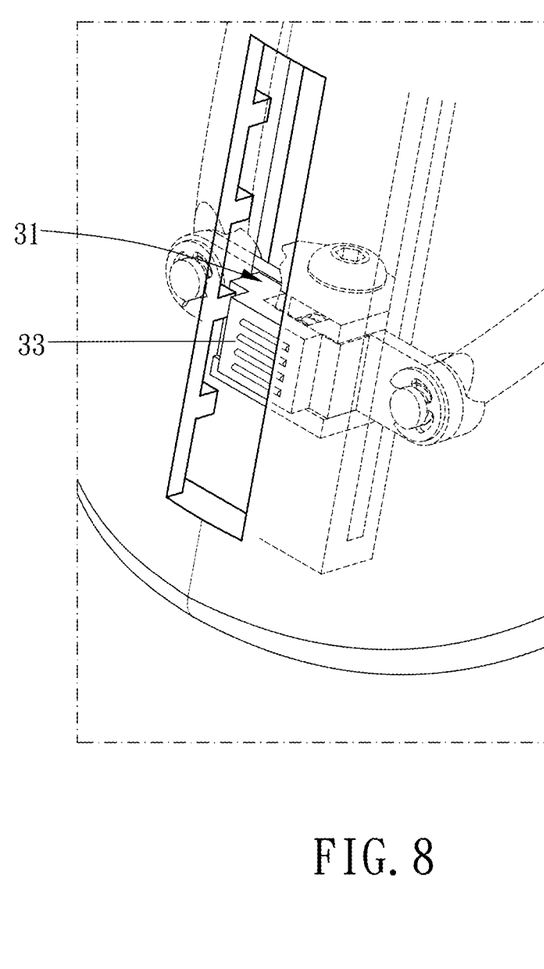

Please refer to FIGS. 1 to 8 for a preferred embodiment of the present invention. An adjustable neck brace 1 includes a neck collar 2, a single positioning member 3, a chin support 4 and at least one connecting member 5.

The neck collar 2 includes a sliding engaging groove 21, and the sliding engaging groove 21 extends in an extension direction and has a first engaging portion 22. The positioning member 3 is attached to the neck collar 2 and movable along the sliding engaging groove 21, the positioning member 3 has a second engaging portion 31, and the second engaging portion 31 is releasably positioningly engaged with the first engaging portion 22. The chin support 4 is relatively movably connected to the neck collar 2. The at least one connecting member 5 connects the positioning member 3 and the chin support 4. Therefore, a user can operate the positioning member 3 to adjust or position a position of the chin support 4 relative to the neck collar 2.

In this embodiment, the positioning member 3 includes a mount portion 32 which is slidably arranged on the neck collar 2 and an operating member 33 which is connected to the mount portion 32, two of the connecting members 5 are connected to the mount portion 32, and the operating portion 33 has the second engaging portion 31. The neck collar 2 further includes two through slots 24 extending in the extension direction and located by two sides of the sliding engaging groove 21, the mount portion 32 includes two wing portions 321, a distal end of each said wing portion 321 is disposed through one of the through slots 24 so as to positioningly restrict the mount portion 32 in a movement range, and the distal end of each said wing portion 321 is connected to one of the connecting members 5 so as to adjust relative positions of the chin support 4 and the neck collar 2 synchronously through each said connecting member 5.

The mount portion 32 includes a base 322 having the two wing portions 321 and two blocking walls 324 connected to two sides of the base 322, the operating member 33 is disposed between the two blocking walls 324, preferably, the two blocking walls 324 are detachably connected to the base 322 so as to assemble/disassemble the positioning member 3 conveniently, an elastic member 323 is disposed between the operating member 33 and the base 322, the elastic member 323 makes the second engaging portion 31 have a tendency to move toward the first engaging portion 22 normally so as to make sure that the second engaging portion 31 can be stably engaged with the first engaging portion 22.

In this embodiment, one of the first engaging portion 22 and the second engaging portion 31 includes at least one recess, and the other of the first engaging portion 22 and the second engaging portion 31 includes at least one protrusion. Specifically, the first engaging portion 22 includes a plurality of recesses 221 arranged along the extension direction in intervals, each said recess 221 has two sides each having a spacing wall 222, the second engaging portion 31 includes an engaging block 311 which is releasably positioningly engaged with one of the recesses 221, and the spacing wall 222 is provided for being positioningly engaged with the engaging block 311.

The neck collar 2 further has two guiding slots 23, the two guiding slots 23 are located by two sides of the sliding engaging groove 21 and extend tiltedly away from the sliding engaging groove 21, one of two end portions of each said connecting member 5 is slidably disposed within one of the guiding slots 23, and the other of the two end portions of each said connecting member 5 is pivoted to one of the wing portions 321 (when in use, an included angle between the wing portion 321 and the connecting member 5 changes, and in order to prevent the connecting member 5 and the wing portion 321 from being bent and damaged, the connecting member 5 and the wing portion 321 are pivoted to each other so that the included angle can be adjusted smoothly in accordance with different requirements). The neck collar 2 has an inner wall which is curved, and the two connecting members 5 are flexible and extend along the inner wall of the neck collar 2 so that when in operation, the connecting member 5 can slidably abut against the inner wall of the neck collar 2 to stabilize the operation. The two blocking walls 324 are opposite to the two spacing walls 222 of one of the recesses 221 and can positioningly restricting the operating member 33 therebetween.

When in use, the user can press and push the operating member 33 to adjust the chin support 4 to a proper position, and one of the two end portions of each said connecting member 5 pushes up or pulls down the chin support 4 along the two guiding slots 23; and when the user stops pressing the operating member 33, the chin support 4 can be relatively positioned.

Figure 9:
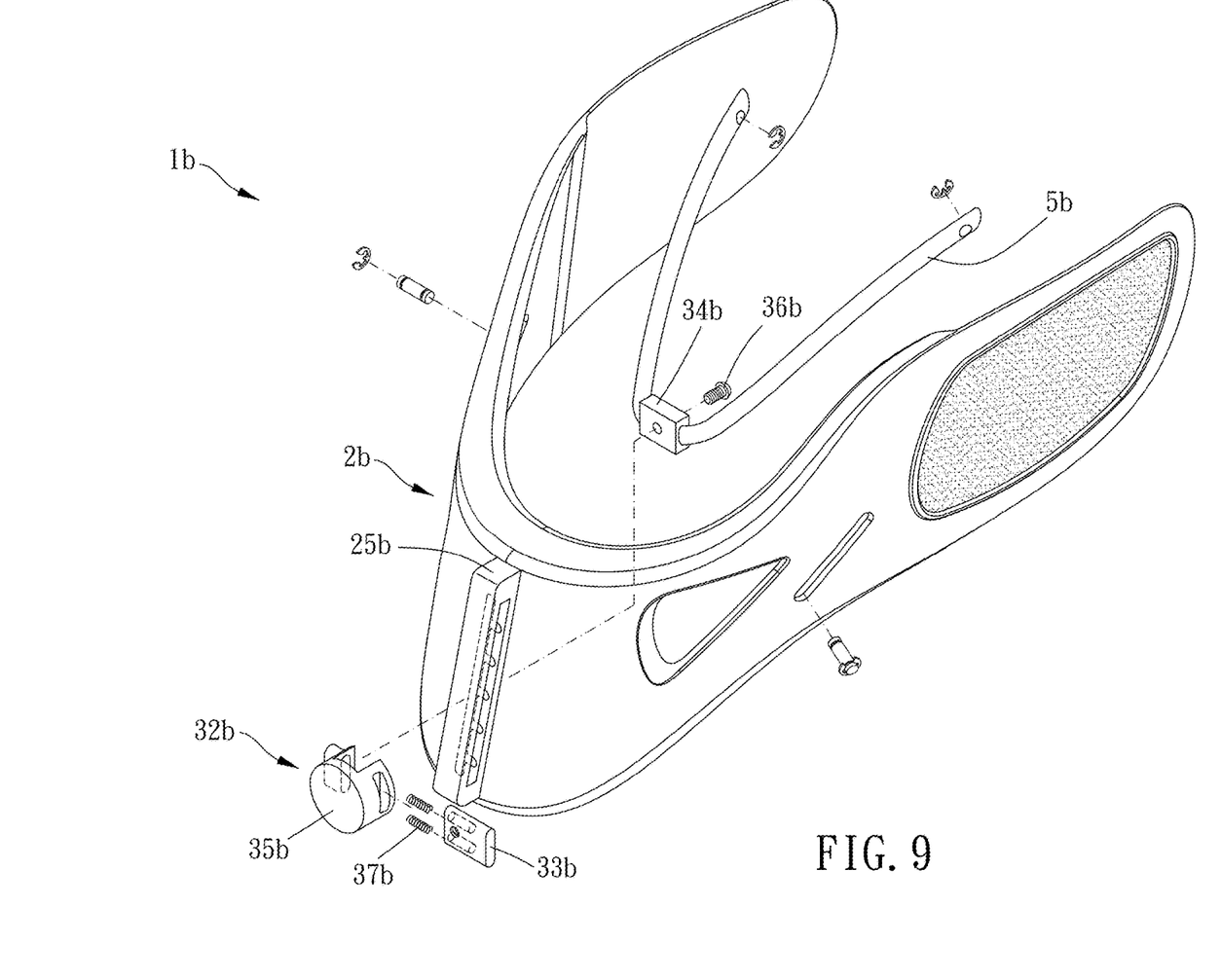
FIG. 9 is a breakdown view of another preferred embodiment of the present invention.
Figure 10:
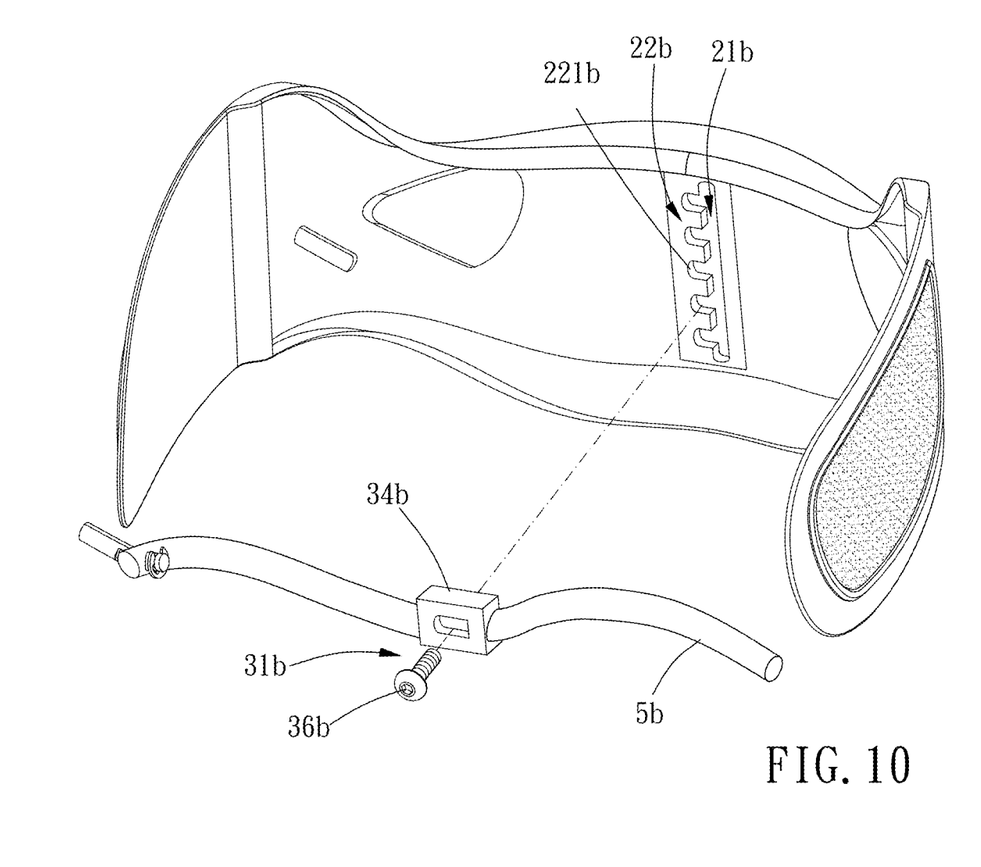
FIG. 10 is a drawing showing another preferred embodiment of the present invention from another perspective.
Figure 11:
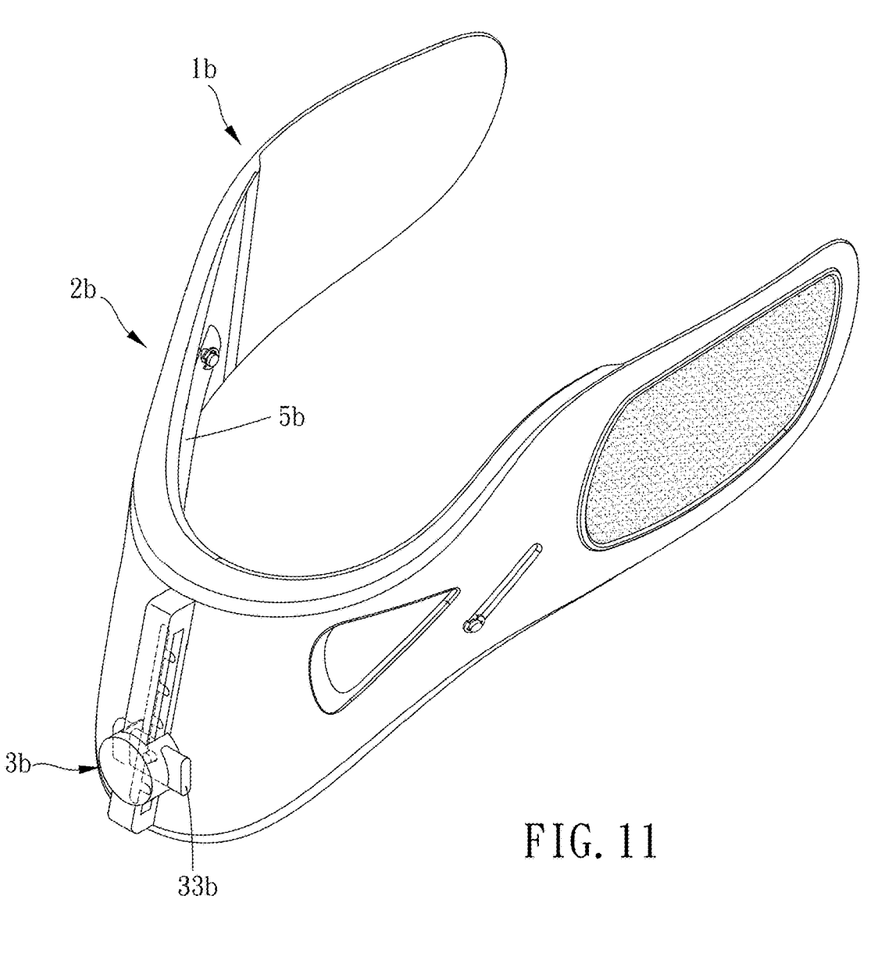
FIG. 11 is a perspective view showing a part of another preferred embodiment of the present invention.
Figure 12:
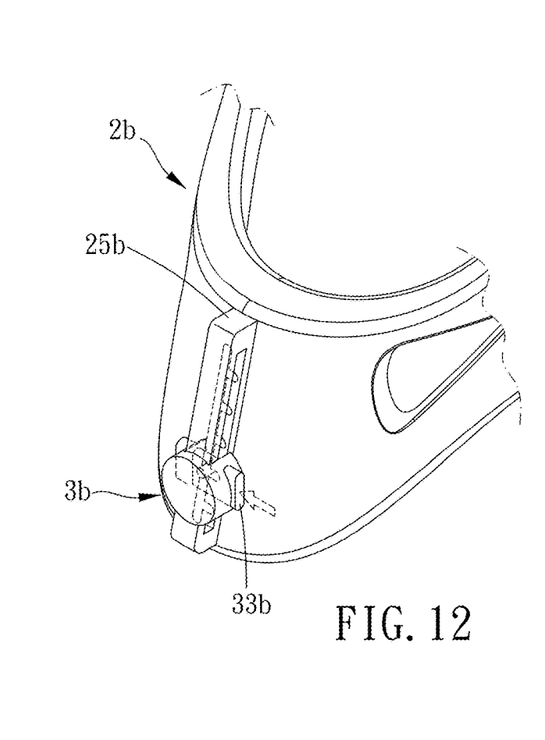
FIG. 12 is partially-enlarged view of FIG. 11.

Please refer to FIGS. 9 to 12 for another embodiment. The first engaging portion 22b includes a plurality of recesses 221b arranged along the extension direction in intervals, and the second engaging portion 31b is releasably positioningly engaged with one of the recesses 221b. The neck collar 2b further includes a sliding seat 25b corresponding to the sliding engaging groove 21b. The positioning member 3b includes a mount portion 32b which is movably arranged on the sliding seat 25b and an operating member 33b which is connected to the mount portion 32b. The mount portion 32b includes a mount body 35b which is saddled on the sliding seat 25b, a position-restricting block 34b which is connected to the at least one connecting member 5b and located by two opposite sides of the sliding engaging groove 21b with the mount body 35b (it is understandable that the at least one connecting member 5b and the position-restricting block 34b may be a structure which is integrally formed or not) and a pin 36b which is disposed through the sliding engaging groove 21b and connects the mount body 35b and the position-restricting block 34b (in other embodiments, the position-restricting block may has a sliding slot, and the pin may be slidably arranged within the sliding slot so that when the user operates the positioning member, the mount body does not need to move horizontally with the pin synchronously, and the positioning member can move smoothly), and the pin 36b has the second engaging portion 31b. The operating member 33b is movably disposed through the mount body 35b and the sliding seat 25b and connected to the pin 36b. An elastic member 37b is disposed between the operating member 33b and the mount body 35b, and the elastic member 37b makes the pin 36b have a tendency to move toward the at least one recess 221b normally. When in use, the user can press the operating member 33b to make the pin 36b detach from the at least one recess 221b and adjust the adjustable neck brace 1b through sliding the mount portion 32b.

In other embodiments, the guiding slot may be arranged vertically; the recess of the first engaging portion may be arranged outwardly, the operating member of the positioning member may be adjusted through pulling outward, and the second engaging portion of the operating member may have a tendency to move toward the first engaging portion normally; the positioning member may be provided with the elastic member and fixedly engaged with the first and second engaging portions through latches.

Given the above, when using the adjustable neck brace, the user only needs to adjust the single positioning member, and the chin support can be adjusted to a proper position through the at least one connecting member. In addition, the adjustable neck brace has a simple structure, and it is easy to be assembled and cost-saving to be manufactured.

While we have shown and described various embodiments in accordance with the present invention, it should be clear to those skilled in the art that further embodiments may be made without departing from the scope of the present invention.

What is claimed is:

1. An adjustable neck brace, including:
 a neck collar, including only one sliding engaging groove which is disposed at middle front of the neck collar, the only one sliding engaging groove extending in a first extension direction and having a first engaging portion;
 only one positioning member, attached to the neck collar and movable along the only one sliding engaging groove, having a second engaging portion, the second engaging portion being releasably positioningly engaged with the first engaging portion;
 a chin support, relatively movably connected to the neck collar;
 at least one connecting member, connecting the only one positioning member and the chin support;
 wherein the positioning member includes a mount portion which is slidably arranged on the neck collar and an operating member which is connected to the mount portion, the at least one connecting member is connected to the mount portion, and the operating portion has the second engaging portion;
 wherein the neck collar further includes two through slots extending in a second extension direction and located by two sides of the only one sliding engaging groove, the mount portion includes two wing portions, a distal end of each said wing portion is disposed through one of the through slots, and the distal end of each said wing portion is connected to one of the connecting members wherein the first extension direction is different than the second extension direction and wherein the mount portion includes a base having the two wing portions and two blocking walls connected to two sides of the base, the operating member is disposed between the two blocking walls, an elastic member is disposed between the operating member and the base, and the elastic member makes the second engaging portion have a tendency to move toward the first engaging portion normally.

2. The adjustable neck brace of claim 1, wherein the two blocking walls are detachably connected to the base.

3. The adjustable neck brace of claim 2, wherein the first engaging portion includes a plurality of recesses arranged along the extension direction in intervals, each said recess has two sides each having a spacing wall, and the second engaging portion includes an engaging block which is releasably positioningly engaged with one of the recesses; the neck collar further has two guiding slots, the two guiding slots are located by the two sides of the only one sliding engaging groove and extend tiltedly away from the only one sliding engaging groove, a number of the at least one connecting member is two, one of the two end portions of each said connecting member is slidably disposed within one of the guiding slots, and the other of the two end portions of each said connecting member is pivoted to one of the wing portions; the neck collar has an inner wall which is curved, and the two connecting members are flexible and extend along the inner wall of the neck collar; the two blocking walls are opposite to the two spacing walls of one of the recesses and capable of positioningly restricting the operating member therebetween.

\* \* \* \* \*